US012653443B2

(12) United States Patent (10) Patent No.: US 12,653,443 B2

Adams (45) Date of Patent: Jun. 16, 2026

(54) SYSTEM FOR TESTING TASTE SENSITIVITY

(71) Applicant: RANVIER HEALTH LIMITED, Bristol (GB)

(72) Inventor: David Adams, Bristol (GB)

(73) Assignee: RANVIER HEALTH LIMITED, Bristol (GB)

( * ) Notice: Subject to any disclaimer, the term of this patent is extended or adjusted under 35 U.S.C. 154(b) by 1296 days.

(21) Appl. No.: 17/282,921

(22) PCT Filed: Oct. 3, 2019

(86) PCT No.: PCT/EP2019/076840

§ 371 (c)(1),
(2) Date: Apr. 5, 2021

(87) PCT Pub. No.: WO2020/070256

PCT Pub. Date: Apr. 9, 2020

(65) Prior Publication Data

US 2021/0401352 A1     Dec. 30, 2021

(30) Foreign Application Priority Data

Oct. 5, 2018     (GB) ..................................... 1816271

(51) Int. Cl.
*A61B 5/00* (2006.01)
*A61B 5/16* (2006.01)

(52) U.S. Cl.
CPC .............. *A61B 5/4017* (2013.01); *A61B 5/16* (2013.01); *A61B 2560/04* (2013.01)

(58) Field of Classification Search
CPC ......... A61B 5/16; A61B 5/165; A61B 5/4017; A61B 2560/04
See application file for complete search history.

(56) References Cited

U.S. PATENT DOCUMENTS

2010/0018331 A1*   1/2010   Tajima .................... B01L 3/508
                                                              73/864.91
2016/0019559 A1*   1/2016   Borack .............. G06Q 30/0201
                                                              705/7.29

(Continued)

FOREIGN PATENT DOCUMENTS

WO         2015021281 A2   12/2015
WO         2018/011566 A1   1/2018

OTHER PUBLICATIONS

Heath TP, Melichar JK, Nutt DJ, Donaldson LF. Human taste thresholds are modulated by serotonin and noradrenaline. J Neurosci. Dec. 6, 2006;26(49):12664-71. doi: 10.1523/JNEUROSCI.3459-06. 2006. PMID: 17151269; PMCID: PMC6674841. (Year: 2006).*

(Continued)

*Primary Examiner* — Niketa Patel
*Assistant Examiner* — Shreya Anjaria
(74) *Attorney, Agent, or Firm* — Troutman Pepper Locke LLP

(57) ABSTRACT

A system for testing a patient's taste recognition and sensitivity. The system includes a sample selector for dispensing taste test samples to the patient, and a test controller configured to determine which taste test sample to dispense to the patient. The test controller is arranged to receive taste test results from the patient associated with the dispensed taste test samples, and determine on the fly which taste test sample to dispense next, based on the received taste test results. Once a plurality of taste test samples have been dispensed to the patient in this manner, the test controller may then determine a taste sensitivity (e.g. threshold) for the patient based on the received taste test results.

17 Claims, 8 Drawing Sheets

(56)　　　　　　References Cited

U.S. PATENT DOCUMENTS

2017/0370759 A1 * 12/2017 Yarnell ................... G01F 23/80
2018/0095659 A1 *  4/2018 Palmer ................. A61B 5/4017

OTHER PUBLICATIONS

International Search Report issued in corresponding International
Patent Application No. PCT/EO2019/076840 dated Mar. 5, 2020.
International Search Report mailed Mar. 15, 2019 in International
Application No. GB1816271.9; 4 pages.
Hirschfeld, R. M. A., "History and evolution of the Monoamine
Hypothesis of Depression" J Clin Psychiatry 61 (suppl 6):4-6
(2000) cited in Specification.

* cited by examiner

SYSTEM FOR TESTING TASTE SENSITIVITY

CROSS REFERENCE TO RELATED APPLICATIONS

The present application is a U.S. National Phase Application under 35 U.S.C. § 371 of International Patent Application No. PCT/EP2019/076840, filed Oct. 3, 2019, which claims priority of United Kingdom Patent Application No. 1816271.9, filed Oct. 5, 2018. The entire contents of which are hereby incorporated by reference.

FIELD OF THE INVENTION

The invention relates to equipment for tasting taste sensitivity, and in particular to a sample dispensing system that enable a blind taste test to be performed using multiple taste modalities.

BACKGROUND TO THE INVENTION

It is known that taste perception in humans (including taste thresholds, perceived taste intensity, perceived pleasantness or unpleasantness of taste) can be altered by different states in both health and disease.

Monoamine neurotransmitters, which include noradrenaline (NA) and serotonin (5-HT), are released from neurones in the brain and contribute to mental state, well-being and perception of the human senses. These same neurotransmitters are used by the taste bud on the tongue in the appreciation of taste. Manipulation of the monoamine neurotransmitters, whether by normal physiological cycles (e.g. menstrual cycle), disease state (e.g. depression) or by medical treatment (e.g. by treatment with antidepressants that modulate monoamine neurotransmission) can lead to changes in mental state and well-being.

The "monoamine theory of depression" suggests that depression is a consequence of diminished circulating monoamine concentrations and hence neurotransmission of NA, dopamine and 5-HT, and/or a reduction in the sensitivity of their receptors (Hirschfeld, 2000. J Clin Psychiatry 61 [Suppl 6]:4-6). Antidepressants used in the treatment of major depression disorder (MDD) target the monoamine neurotransmitters (e.g. NA and 5-HT).

SUMMARY OF THE INVENTION

The present invention arises out of the surprising finding that patients with previously undiagnosed and untreated clinical depression exhibit an acute response to medical treatment (e.g. with a medicament that increases monoamine neurotransmission) when taste recognition profiles are measured, despite a lack of immediate effect on the patient's symptoms. This led to the realisation that measuring a patient's taste sensitivity can be used as an indicator of whether they are suffering from depression because of an imbalance in neurotransmitters (e.g. NA and 5-HT). A patient's taste sensitivity may also be used to assess whether treatment with antidepressants targeting those neurotransmitters is likely to be effective.

At its most general, the invention provides a system for testing a patient's taste recognition and sensitivity. The system includes a sample selector for dispensing taste test samples to the patient, and a test controller configured to determine which taste test sample to dispense to the patient. The test controller is arranged to receive taste test results from the patient associated with the dispensed taste test samples, and determine which taste test sample to dispense next, based on the received taste test results. Once a plurality of taste test samples have been dispensed to the patient in this manner, the test controller may then determine a taste sensitivity (e.g. threshold) for the patient based on the received taste test results.

In this manner, the patient's response to a taste test sample can be used by the test controller in an automated feedback loop to dynamically adapt the subsequently dispensed test samples. The invention may permit the selection of test samples to be adapted whilst preserving the "blind" nature of the test, e.g. where the patient (i.e. person being tested) and tester (i.e. person administrating the test, if present) are unaware of the nature of the test samples that are selected. The invention thus provides an efficient and repeatable testing set up that enables a patient's taste sensitivity to be determined with confidence.

According to a first aspect of the invention, there may be provided a sample dispensing system for testing a patient's sensitivity to a plurality of taste modalities, the system comprising: a sample selector comprising: an array of tasting samples, each tasting sample being one of a plurality of tasting modalities at a predetermined concentration, and a selection mechanism configured to present one of the tasting samples from the array of tasting samples; a test controller configured to generate a sequence of sample indicators for operating the selection mechanism to present a sequence of tasting samples in which the order of the tasting modalities is mixed; and a patient terminal configured to communicate a patient response to each presented tasting sample to the test controller, wherein the test controller is configured to adapt the sequence of sample indicators on the fly based on each received patient response. As discussed in more detail below, the test controller may operate independently of the sample selector and patient terminal (e.g. at a remote location), whereby knowledge of the nature of the tasting sample that is associated with a given sample indicator is not present at the test site (e.g. to any of the patient, sample selector device and a test supervisor, if present). This ensures that the test is conducted "blind", whilst also permitting the sequence in which samples are presented to be adapted reactively to previous responses by the patient so that the test can be administered efficiently and effectively.

The test controller may be configured to determine a subsequent sample indicator in the sequence of sample indicators for a given tasting modality based on the patient's response to a previous tasting sample having that tasting modality. In other words, the sequence may be built up as the test progresses. For each modality, the test controller may be arranged to determine a subsequent sample indicator based on a previous response from the patient for that modality. Each modality can therefore be considered as having its own stream of sample indicators, which the test controller interweaves so that the order in which modalities are presented to the patient are mixed. The mixing may be done in a random manner, e.g. based on a pseudo random selection mechanism in the test controller.

The test controller may comprise a computing device having a processor arranged to execute computer readable instructions to perform the functions set out herein. The test controller may include a memory storing a correspondence table that matches each sample indicator to the tasting modality and the predetermined concentration of the tasting sample in the array that corresponds to that sample indicator.

In this manner, information relating to the modality of the samples and their concentrations need not be kept at a testing site, so that the taste test can be performed "blind" by the patient and tester (if present).

The test controller may be configured to determine the subsequent sample indicator in the sequence of sample indicators for a given tasting modality by selecting a sample indicator for the given tasting modality that has a higher predetermined concentration if the patient response incorrectly identified the previous sample for the given tasting modality, or selecting a sample indicator for that tasting modality that has a lower predetermined concentration if the patient response correctly identified the previous sample for the given tasting modality. Thus, the test controller may select the next sample for a given tasting modality based on the patient's response to the previous sample of that tasting modality. By selecting samples for a given taste modality in this manner, the test controller may be able to determine a minimum concentration for that modality to which the patient is sensitive.

In some embodiments, the test controller may be configured to judge whether or not each received patient response correctly identifies a tasting modality of the corresponding presented tasting sample. For example the test controller may be configured to compare the patient's response with the tasting modality of the tested sample. Where the test controller stores a correspondence table, this may be done by looking up the relevant sample in the correspondence table.

The test controller may be configured to communicate the sample indicators in sequence one-by-one. For example, the next sample indicator may not be communicated until a patient response for the previous sample has been received by the test controller. In this manner, the test controller may determine the next sample indicator based on the patient response for the previous sample, and then communicate the next sample indicator. This may enable the sequence of indicators to be adapted in real-time by the test controller based on responses received from the patient terminal. Communicating sample indicators one-by-one may also avoid a risk of errors in the test, as this may serve to ensure that samples are dispensed in the correct order.

In some embodiments, the sequence of sample indicators may mix the tasting modalities in a pseudo-random order. For example, the sequence may include an indicator for a first sample of a first tasting modality. Then, the next sample indicator in the sequence may correspond to a sample of a pseudo-randomly selected tasting modality (from a plurality of tested tasting modalities). This may avoid the patient tasting a large number of samples from the same tasting modality in a row, which could lead to the patient becoming used to that tasting modality, or which could lead to the patient guessing the tasting modality. In this manner, accuracy of the test may be improved. The order of the tasting modalities may be "pseudo-random" in that it is generated randomly whilst avoiding certain predetermined combinations of tasting modalities. For example, the inventors have found that it is preferable not to test a sweet tasting modality immediately after testing a sour tasting modality, as the patient's sensitivity to the sweet tasting modality may be reduced after the sour tasting modality. Thus, in one embodiment, the tasting modalities may be mixed in a pseudo-random order which avoids testing the sweet taste modality after the sour taste modality.

The patient terminal may be a network-enabled computing device, and the test controller may comprise a remote server. Thus, the patient terminal and the test controller may be in communication over a network, e.g. a local network or the internet. For example, the patient terminal may be a desktop computer, laptop, tablet computer or smartphone.

The patient terminal may be configured to run a taste testing application that is controlled by the test controller via the network. In this manner, the test controller may control information that is displayed by the patient terminal, and communicate with the patient terminal (e.g. to send and/or receive data). Thus, during a taste test, the test controller may cause the patient terminal to display a series of different tasting modalities. The patient may then select a tasting modality on the patient terminal based on a sample they have tasted, and the terminal may transmit the patient's response to the test controller. The remote server may be a computer executing an algorithm for controlling the taste test.

The sample selector may include a communication module in communication with the test controller to receive the sequence of sample indicators. The sample selector may be in communication with the test controller via a direct connection (e.g. via USB) or via a network, e.g. a local network or the internet. In this manner, the test controller may communicate the sequence of sample indicators to the sample selector, so that the sample selector can be controlled to present the samples to the patient according to the sequence.

The selection mechanism may be automatically controllable based on the received sequence of sample indicators. In this manner, the process of selecting samples and presenting samples to the patient may be fully automated. The selection mechanism may include a motorised actuator (e.g. step motor or the like) that is controllable based on the sequence of sample indicators. The motorised actuator may then actuate the selection mechanism based on the sequence of sample indicators, in order to sequentially present the relevant samples to the patient. The sample selector may include a local controller (e.g. microprocessor) which is arranged to receive the sequence of sample indicators from the test controller and control the motorised actuator accordingly. In some cases, the test controller may be configured to transmit an instruction to the sample selector when the test controller determines that it is time to move to the next sample (e.g. when the patient has completed a test with a current sample). Then, when the sample selector receives the instruction, the selecting mechanism may be automatically controlled to present the next sample to the patient.

In some embodiments, the sample dispensing system may further comprise a tester terminal configured to receive the sequence of sample indicators, and the selection mechanism may be manually controllable based on the sequence of sample indicators received at the tester terminal. Thus, a tester (e.g. a person who is administering the taste test) may read the received sequence of sample indicators from the tester terminal and control the selection mechanism to present the corresponding samples to the patient. The tester terminal may be similar to the patient terminal discussed above. In particular, the tester terminal may be a network-enabled computing device (e.g. tablet computer, smartphone, etc.) that is in communication with the test controller, either directly (e.g. via USB) or over a network (e.g. local network or the internet). The tester terminal may be configured to run a taste testing application that is controlled by the test controller, so that the test controller can cause relevant information and/or options to be presented on the tester terminal.

The selection mechanism may be configured to manipulate the array of tasting samples to move the one of the tasting samples that is to be presented to a sampling location on the sample selector. Thus, the selection mechanism may enable a selected one of the tasting samples from the array to be presented at the sampling location. The sampling location on the sample selector may be a location that is accessible to the patient, so that the patient can perform a taste test with the selected sample. The selection mechanism may include any suitable mechanism for manipulating an array of samples and selecting a particular tasting sample from the array of samples.

In some embodiments, the array of tasting samples may comprise a circle of tasting samples arranged on a rotatable carousel, and the sampling location may be at a given angular position on the sample selector. The rotatable carousel thus acts as a selection mechanism for the sample selector. The rotatable carousel may be rotatable relative to the sampling location, such that the carousel can be rotated to present a desired tasting sample at the sampling location. A tasting sample may be presented at the sampling location when its angular position is aligned with the angular position of the sampling location. This may facilitate presenting a selected tasting sample at the sampling location, as the presented sample may be controlled based on an angular position of the carousel relative to the sampling location. The angular position may, for example, be controlled automatically by a motorised actuator, or manually by a tester. In some cases, a position sensor may be provided to determine the angular position of the carousel, to facilitate selection of a tasting sample.

The sample selector may include a cover arranged to hide the array of testing samples except at the sampling location. In other words, the lid may be configured to cover all of the testing samples except for a testing sample located at the sampling location. In this manner, only a testing sample at the sampling location may be accessible to the patient. This may ensure that the patient uses the correct tasting sample during a taste test. The sampling location may be provided by an aperture in the lid, through which the sample at the sampling location is accessible.

In some embodiments, each tasting sample in the array of tasting samples may have a sample indicator and a confirmation code associated with it, and the sample indicator and confirmation code for a given tasting sample may be readable when that tasting sample is at the sampling location. In this manner, the sample indicator and confirmation code may be used to select a tasting sample and verify that the correct sample is being presented at the sampling location. The sample indicator associated with a tasting sample may correspond to a position of the tasting sample within the array of tasting samples. Thus, the sample indicator may be used to locate a particular tasting sample and present it at the sampling location. The confirmation code associated with a tasting sample may be a unique code associated with that tasting sample. The confirmation code may thus be used to confirm that the correct tasting sample is presented at the sampling position.

The sample indicator and/or confirmation code may be machine readable. For example, the sample selector may include a reader (or sensor) arranged to read the sample indicator and/or confirmation code of a tasting sample at the sampling location. Alternatively, the sample indicator and/or confirmation code may be read by a tester administering the taste test. In such a case, the sample selector may include a reading location for reading the sample indicator and/or confirmation code of the tasting sample at the sampling location. For example, the sample selector may include a window through which the sample indicator and/or confirmation code of the tasting sample at the sampling location is visible. The reading location may be displaced from the sampling location. In this manner, the indicator and/or confirmation code of the presented tasting sample may not be visible to the patient, who is typically located next to the sampling location. The indicator and/or confirmation code may then be read by a tester who is administering the test. For example, where the sample selector includes a rotatable carousel, the reading location may be at a different angular position compared to the sampling location.

The sample dispensing system may be configured such that the confirmation code is communicated to the test controller before the patient terminal allows the patient to enter a response (e.g. before the patient is allowed to select a tasting modality identified by the patient). The test controller may store a table associating individual tasting samples with their respective confirmation codes. In this manner, when the test controller receives the confirmation code, the test controller may verify that the correct tasting sample is presented at the sampling location. Once the tasting sample is confirmed to be the correct one, the test controller may cause the patient terminal to request a response from the user. This may ensure that that the correct tasting samples are used during the taste test. Where the confirmation code of the tasting sample at the sampling location is machine readable, the sample selector may be configured to automatically read the confirmation code and transmit it to the test controller. Where the confirmation code is readable by a tester, the tester may be prompted by the tester terminal to enter the confirmation code, which is then transmitted to the test controller for verification.

In some embodiments, the array of tasting samples may be disposed in a cassette that is removably mountable in the selection mechanism. This may facilitate loading tasting samples into the sample selector, as the tasting samples may be pre-loaded into the cassette before the cassette is mounted in the selection mechanism. This may also enable tasting samples to be rapidly exchanged, by exchanging cassettes, e.g. so that multiple taste tests may be performed in rapid succession. The cassette may include an array of slots or holders for receiving tasting samples. The cassette may be a multi-part cassette, e.g. the cassette may include multiple separate parts that fit into different locations in the selection mechanism. The different cassette parts may have indicia thereon, to ensure that the different parts are mounted in a correct location in the selection mechanism.

The cassette and selection mechanism may comprise cooperating engagement features, whereby the cassette is mountable in the selection mechanism in a predetermined orientation. The cooperating engagement features may thus ensure that the cassette is mounted in the selection mechanism in the predetermined orientation, which in turn may ensure that the array of tasting samples is in a predetermined orientation. This may facilitate control of the selection mechanism for presenting a desired tasting sample to the patient. For example, where the sample indicator for a particular tasting sample correspond to a position of that tasting sample in the array, ensuring a correct orientation of the array may enable a desired sample to be selected based on the sample indicator. The predetermined orientation may be defined relative to a reference frame of the selection mechanism. Alternatively, the predetermined orientation may be defined relative to some external reference (e.g. a reference frame of the sample selector relative to which array is movable). The predetermined orientation may define a starting position of the selection mechanism.

The cooperating engagement features may include a first set of engagement features on the cassette and a second set of engagement features on the selection mechanism, the first set of engagement features being arranged to engage the second set of engagement features when the cassette is mounted in the selection mechanism. For example, the first set of engagement features may include a set of protrusions on a surface of the cassette, and the second set of engagement features may include a set of grooves on the cassette arranged to receive the protrusions. The cooperating engagement features may be arranged such that the cassette is only mountable in the selection mechanism in the selection mechanism. This may reduce the risk of errors when mounting the cassette in the selection mechanism.

The cassette may include an identifier for communicating to the test controller, and the test controller may be arranged to determine a correspondence table for the array in the cassette using the identifier, wherein the correspondence table is a data structure that matches each sample indicator to the tasting modality and the predetermined concentration of the tasting sample in the array that corresponds to that sample indicator. Thus, at the beginning of a taste test, the identifier may be communicated to test controller, which may then determine the correspondence table based on the identifier. This may enable the same test controller to be used for multiple different taste tests, e.g. tests using different arrays of tasting samples, as the test controller can automatically generate a correspondence table at the beginning of the test. The identifier may, for example, include information relating to a type of taste test that is to be performed, or a tasting sample batch which is being used. The test controller may look up (either in local memory or from a separate server) data for an array of tasting samples associated with the received identifier. Based on the looked-up data, the test controller may then determine the correspondence table. As discussed above, the correspondence table may be used by the test controller to generate the sequence of sample indicators.

The sample selector may be configured to obtain the identifier (e.g. via a reader or a sensor) when the cassette is mounted in the selection mechanism, and to transmit the identifier to the test controller. Alternatively, a tester may enter the identifier via a tester terminal, which then transmits the identifier to the test controller.

The sample selector discussed above may be an independent aspect of the present disclosure. Thus, according to a second aspect of the invention, there is provided a sample selector device for presenting tasting samples to a patient, the sample selector device comprising: an array of tasting samples, each tasting sample being one of a plurality of tasting modalities at a predetermined concentration, and a selection mechanism configured to present one of the tasting samples from the array of tasting samples at a sampling location on the device, wherein the selection mechanism is configured to manipulate the array of tasting samples, whereby each tasting sample is selectively movable to the sampling location, wherein each tasting sample in the array of tasting samples has an associated sample indicator, and wherein the selection mechanism is operable to locate a given tasting sample at the sampling location based on a received sample indicator. The sample selector may be arranged such that only one tasting sample occupies the sampling location. In this manner, it may be possible to ensure that the correct tasting sample is presented to the patient.

The array of tasting samples may comprise a circle of tasting sample arranged on a rotatable carousel, and the sampling location may be at a given angular position on the sample selector.

The sample selector device may further comprise a cover arranged to hide the array of testing samples except at the sampling location.

Each tasting sample in the array of tasting samples may have a sample indicator and confirmation code associated with it, and the sample indicator and confirmation code for a given tasting sample may be readable when that tasting sample is at the sampling location.

The sample selector device may further comprise a communication module configured to receive a sample indicator from a remote server, and to transmit a confirmation code for a tasting sample at the sampling location to the remote server.

The selection mechanism may comprise a motor for automatically moving a tasting sample to the sampling location based on the received sample indicator.

The array of tasting samples may be disposed in a cassette that is removably mountable in the selection mechanism.

The cassette and selection mechanism may comprise cooperating engagement features, whereby the cassette is mountable in the selection mechanism in a predetermined orientation.

Herein, a "tasting sample" (also "taste test sample" or "sample") may refer to a sample that is suitable for use in a taste test. For example, a tasting sample may include an aqueous solution of a chemical compound at a given concentration. The chemical compound may correspond to a particular taste modality.

Herein, a "tasting modality" (also "taste modality" or "modality") may refer to a taste type, e.g. sweet, salt, sour, bitter.

During a taste test, a user may taste a tasting sample at associated with a given tasting modality and at a given concentration, e.g. by imbuing a cotton bud with the tasting sample and placing the cotton bud on the tip of their tongue. The user may then be asked to indicate whether they recognise the tasting modality of the tasting sample they have tasted.

BRIEF DESCRIPTION OF THE DRAWINGS

Drawings of the invention are discussed below with reference to the accompanying drawings.

DETAILED DESCRIPTION

Figure 1:
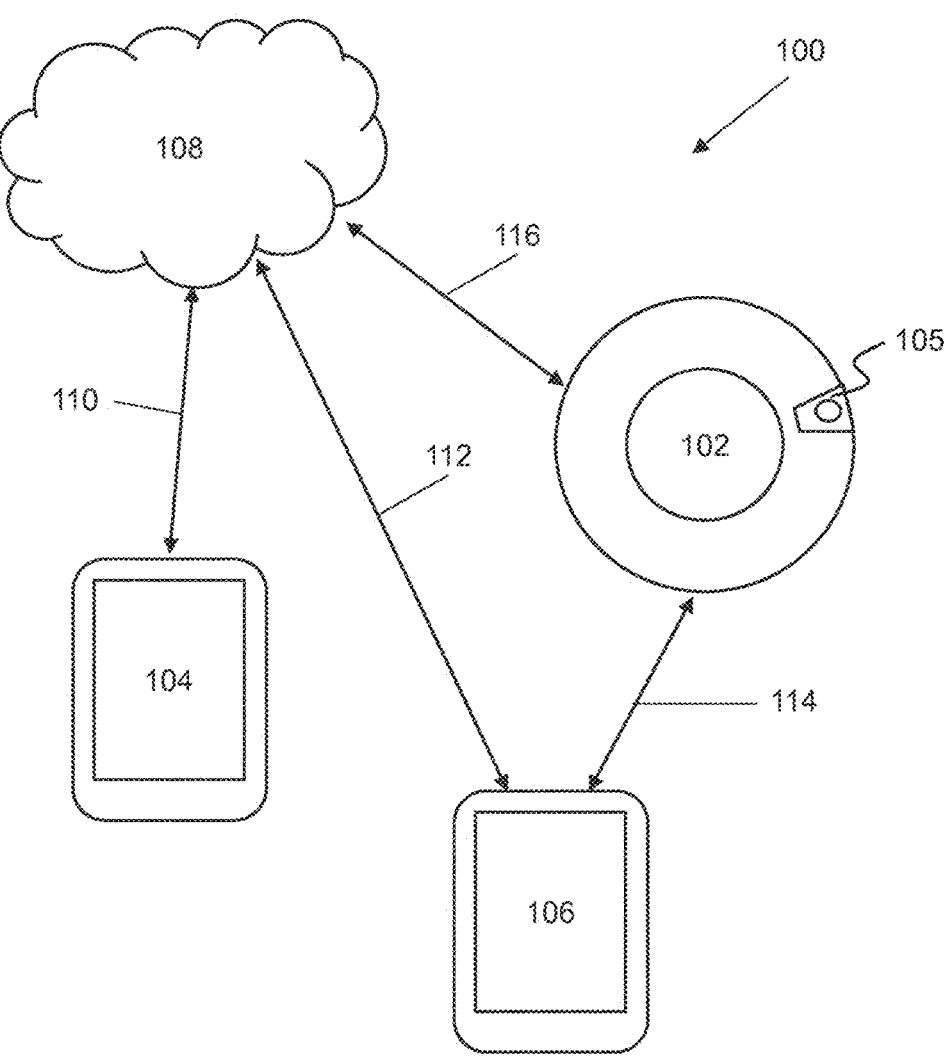
FIG. 1 is a schematic diagram of a taste test system that is a drawing of the invention.

FIG. 1 shows a diagram of system 100 for testing a patient's taste recognition and sensitivity that is an embodiment of the invention. The system 100 is configured to test the patient's sensitivity to four different taste modalities, which are sweet, salt, sour and bitter. A control modality (e.g. water) is also used in the testing. In other examples, the system may be configured to test sensitivity for more, fewer, or different taste modalities.

The system 100 includes a sample selector 102. The sample selector 102 stores a plurality of taste test samples (not shown) which are to be used during a taste test. The plurality of taste test samples may include taste test samples corresponding to different taste modalities (e.g. sweet, salt, sour, bitter) and which are at different concentrations. The sample selector 102 includes a selecting mechanism for selecting a specific one of the stored taste test samples and making the selected taste test sample available at a sampling location 105 for tasting. In this manner, a patient (i.e. a person taking the taste test) may taste the taste test samples in a desired order.

Each taste test sample is stored in a respective sample position within the sample selector 102, e.g. the sample positions may be numbered. The sample selector 102 includes an indicator for indicating the currently selected sample position, to enable a tester to select a desired taste test sample. Additionally, each of the taste test samples may be associated with a unique confirmation code that is displayed when the taste test sample is selected, so that the tester may further verify that the correct sample has been selected. An example sample selector is described below in relation to FIGS. 2 to 9.

The system 100 further includes a patient terminal 104 and a tester terminal 106 which are both communicatively coupled over a network to a remote server 108. The remote server 108 may be in the cloud, whereby the network includes the internet. However, in other examples the remote server 108 may be accessible by the patient terminal 104 and tester terminal over other types of network, e.g. local area network. The communication link to the remote server 108 is preferably wireless for convenience.

The patient terminal 104 may be any suitable computing device capable of communicating with the remote server 108 and running a taste testing application thereon. The patient terminal 104 includes a display for displaying information, and a user interface (e.g. touchscreen, mouse, keyboard) for receiving inputs from a patient. For example, the patient terminal 104 may be a desktop computer, laptop, tablet computer or smartphone. The patient terminal 104 is communicatively coupled to the remote server 108 via a network connection 110, e.g. via the internet. The patient terminal 104 may be connected to the internet via a wired or wireless connection.

Similarly, the tester terminal 106 may be any suitable computing device capable of communicating with the remote server 108 and running a taste testing application thereon. The tester terminal 106 includes a display for displaying information, and a user interface (e.g. touchscreen, mouse, keyboard) for receiving inputs from a tester (i.e. a person administering the taste test). For example, the tester terminal 106 may be a desktop computer, laptop, tablet computer or smartphone. The tester terminal 106 is communicatively coupled to the remote server 108 via a network connection 112, e.g. via the internet. The tester terminal 106 may be connected to the internet via a wired or wireless connection. In some embodiments, the tester terminal 106 may be communicatively coupled to the sample selector 102 via communication link 114. Communication link 114 may be a wired connection (e.g. USB) or a wireless connection (e.g. Bluetooth, WiFi). In some cases, communication link

114 may be provided by a local network (not shown). In this manner, the tester terminal may transmit instructions to the sample selector 102 and/or receive data from the sample selector 102.

The remote server 108 may be a conventional remote server arranged to receive data from, and transmit data to, the patient terminal 104 and the tester terminal 106 over the internet. The remote server 108 includes software installed thereon for controlling a taste test based on data received from the patient terminal 104 and the tester terminal 106, as discussed in more detail below. In this manner, the remote server 108 acts as a taste test controller. In some cases, the remote server 108 may be communicatively coupled 108 to the sample selector 102 via a network connection 116 (e.g. over the internet), so that it may receive data from the sample selector 102 and/or transmit instructions to the sample selector 102. In some embodiments (not shown), the remote server 108 may be implemented by a computer which is connected to a local network, e.g. the patient terminal 104, tester terminal 106 and sample selector 102 may communicate with the remote server 108 over a local network.

The patient terminal 104 and tester terminal 106 may each include a processor that executes an app or similar software for running the taste test. The app may be configured to establish communication with the remote server 108. The control of the taste testing process may be performed at the remote server 108, e.g. based on information delivered from the patient terminal 104. The patient terminal 104 and tester terminal 106 may not analyse or locally process received inputs. They may instead operate to send information to the remote server 108 and simply display information received from the remote server. The patient terminal 104 and the tester terminal 106 may thus be remotely controlled, through the app, by the remote server 108, e.g. the remote server 108 may control information that is displayed by the patient terminal 104 and the tester terminal 106, and/or control an interface presented to users of the patient terminal 104 and the tester terminal 106.

The remote server 108 stores a list of taste test samples that are stored in the sample selector 102, including information relating to the taste modality and concentration of each taste test sample. The list of taste test samples in the remote server 108 associates each taste test sample with a respective position in the sample selector 102 and with a respective confirmation code. Neither the indicator on the sample selector 102, nor the confirmation codes associated with the taste test samples include information regarding the taste modality of the corresponding taste test sample, or its concentration. In this manner, the system 100 may be used to perform a taste test where both the tester and the patient are "blind" with regards to the taste test samples being tested, as all of the information relating to the nature of the samples is stored in the remote server 108. This may improve accuracy of the taste test, e.g. by avoiding any bias on the part of the tester or patient.

The knowledge of the location of the samples within the sample selector 102 may be achieved by placing the samples into particular locations within the dispenser itself or by mounting within the sample selector a cartridge, cassette, or other carrying structure that is pre-loaded with the samples in a particular (known) order. The indicators (e.g. sample numbers used to indicate which sample is to be selected) may be on the cartridge or the sample selector. In the latter case, the cartridge may be configured so that is fits within the sample selector in only one orientation, so that the correspondence between the sample indicators on the sample selector and the actual samples in the cartridge is fixed.

In a development of the invention, a plurality of cartridges each having a different predetermined order of samples may be used. In this example, the cartridge may have an identifier (e.g. a machine readable label such as a bar code or QR code) that can be communicated to the remote server 108 (e.g. by the patient terminal 104 or tester terminal) as part of the test set up.

We will now briefly describe an example operation of the system 100. Before the test begins, the patient tastes an identified sample of each of the modalities at a high concentration, so they are aware of how each modality tastes.

After the preliminary identified samples, the test begins properly by the remote server 108 causes the app on the tester terminal 106 to display an instruction for the tester to select a first sample from the plurality of samples stored in the sample selector 102. For example, the remote server 108 may cause the tester terminal 106 to display an indicator position of the sample selector 102 corresponding to the desired taste test sample. The tester may then actuate the selecting mechanism of the sample selector 102, until the indicator on the sample selector indicates that the desired sample has been selected.

The taste testing application on the tester terminal 106 then prompts the tester to enter the displayed confirmation code associated with the selected sample, to confirm that the correct taste test sample has been selected. The tester terminal 106 transmits the entered confirmation code to the remote server 108, which compares the confirmation code with a stored confirmation code corresponding to the desired taste test sample. If the entered confirmation code matches the stored confirmation code, the taste testing application on the tester terminal 106 may indicate that the taste test can proceed. Otherwise, the taste testing application on the tester terminal 106 instructs the tester to try again until the correct confirmation code is found. In this manner, it is possible to ensure that the correct taste test sample is used for the taste test.

Following confirmation that the correct taste test sample has been selected, the patient terminal 104 displays multiple selectable options corresponding to the different taste modalities that are being tested (e.g. sweet, salt, sour, bitter). The patient then tastes the selected taste test sample, e.g. by dipping a cotton bud into the sample and placing the cotton bud on the tip of their tongue. The patient then indicates which taste modality they have identified, by selecting one of the options displayed on the patient terminal 104. The patient terminal 104 then transmits the patient's selection to the remote server 108.

The remote server 108 receives the patient's selection, and uses it as an input in an algorithm for determining a second taste test sample to be tested by the patient. Once the remote server 108 has determined the second taste test sample, the remote server 108 causes the tester terminal 106 to display an instruction for the tester to select the second sample from the plurality of samples stored in the sample selector 102. The process described above in relation to the first sample is then performed for the second sample. This process may be repeated for multiple samples, until the remote server 108 is able to determine the patient's taste sensitivity and recognition based on the patient's responses.

In another example operation of the system 100, the remote server 108 may control the sample selector 102 directly, via network connection 116. In this case, the sample selector 102 may include a motor, e.g. a step motor, for actuating the selecting mechanism of the sample selector

102. The sample selector 102 may further include a local controller (e.g. a microprocessor) for controlling the motor based on instructions received from the remote server 108. In this manner, the remote server 108 may transmit instructions to the sample selector 102 directly, to control which taste test sample is selected. Thus, in this scenario the tester need not operate the selecting mechanism of the sample selector, and selection of the sample is performed automatically based on instructions transmitted from the remote server 108 to the sample selector 102.

Once the remote server 108 has caused the sample selector 102 to select a particular sample, the tester may read the displayed confirmation code associated with the selected sample. The tester may then enter the confirmation code in the taste testing application on the tester terminal 106, so that the remote server can verify that the correct taste test sample has been selected, as discussed above. Alternatively, the sample selector 102 may include a sensor for reading the confirmation code of the selected sample. For example, the confirmation code may be in the form of a bar code or other machine-readable indicia, and the sample selector may include a barcode reader arranged to read the barcode of the selected sample. In such a case, the sample selector may automatically transmit the confirmation code associated with the selected taste test sample, either directly or via the tester terminal 106. In yet further embodiments in which selection of the sample is automated, the cross check confirmation code discussed above need not be used. In this scenario the tester may have a supervisory role, or may be absent altogether.

Figure 2:
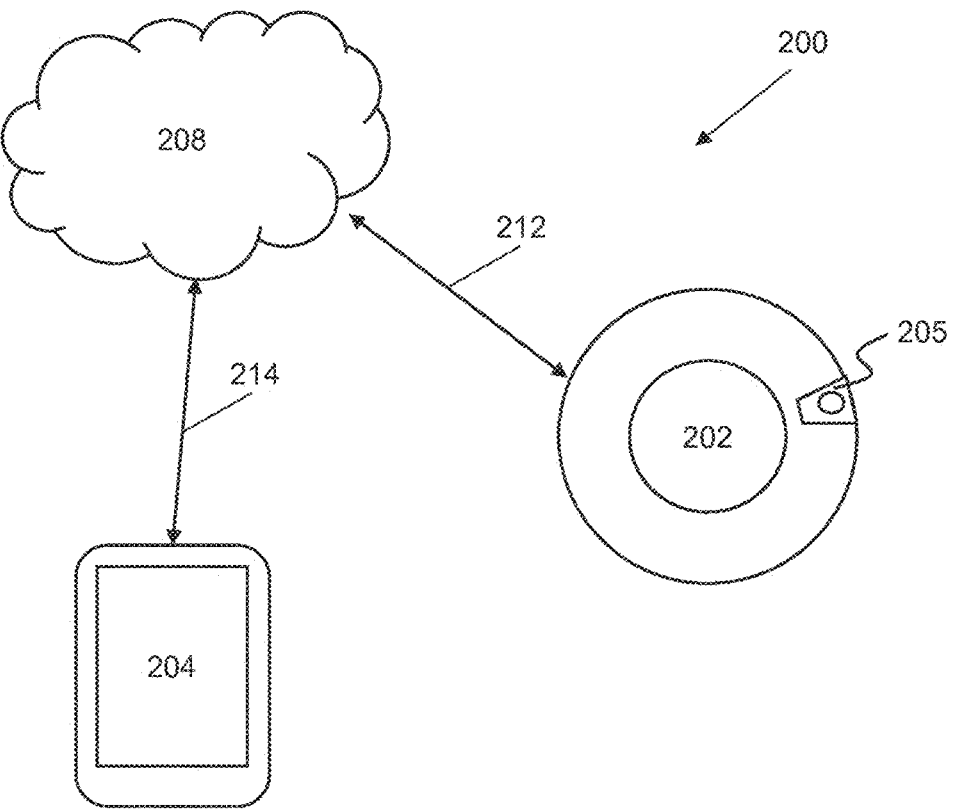
FIG. 2 is a schematic diagram of a taste test system that is another drawing of the invention.

FIG. 2 shows a diagram of system 200 for testing a patient's taste recognition and sensitivity that is another embodiment of the invention. System 200 enables a fully automated taste test to be performed, i.e. a patient may perform the test by themselves and there is no need for a tester to administer the test.

The system 200 is similar to system 100 described above, except that it does not include a tester terminal 106. Functions which are performed by the tester terminal 106 in system 100, are instead performed by sample selector 202 in system 200. The system 200 includes sample selector 202 and a patient terminal 204 which are both communicatively coupled to a remote server 208, via network connections 212 and 214, respectively. The patient terminal 204 is similar to patient terminal 104 described above, and fulfils the same functions as patient terminal 204.

The sample selector 202 of system 200 is similar to the sample selector 102 described above. In particular, the sample selector 202 stores a plurality of taste test samples for use in a taste test, and has a selecting mechanism for selecting one of the stored samples (e.g. by presenting it at a sampling location 205). The selecting mechanism is controlled by the remote server 208, i.e. the remote server 208 may transmit instructions to the sample selector 202 to cause the selecting mechanism to select a particular sample (e.g. based on a storage position of the sample in the sample selector 102). For example, as mentioned above, the sample selector 202 may include a motor for actuating the selecting mechanism, and a local controller for controlling the motor based on instructions received from the remote server 208. Additionally, the sample selector 202 is configured to transmit the confirmation code associated with the selected sample to the remote server 208, so that the remote server 208 can verify that the correct sample has been selected. As mentioned above, the sample selector 202 may include a sensor arranged to read the confirmation code of the selected sample.

The remote server 208 is similar to remote server 108 described above, and fulfils the same functions.

In operation, the remote server 208 transmits an instruction to the sample selector 202 to select a first sample. For example, the remote server 208 may instruct the motor in the sample selector to move the selecting mechanism to a position corresponding to the first taste test sample (based on information stored in the remote server 208 relating to the storage positions of the samples). The sample selector 202 receives the instructions and actuates the selecting mechanism to select the sample at the relevant position. The sample selector then reads the confirmation code of the selected sample and transmits it to the remote server 208. Upon receipt of the transmitted confirmation code, the remote server 208 confirms that the correct sample has been selected. If not, the remote server instructs the sample selector 202 to actuate the selecting mechanism until the correct sample is found.

Following confirmation that the correct taste test sample has been selected, the patient terminal 204 displays multiple selectable options corresponding to the different taste modalities that are being tested (e.g. sweet, salt, sour, bitter). The patient then tastes the selected taste test sample, e.g. by dipping a cotton bud into the sample and placing the cotton bud on the tip of their tongue. The patient then indicates which taste modality they have identified, by selecting one of the options displayed on the patient terminal 204. The patient terminal 204 then transmits the patient's selection to the remote server 208.

Similarly to system 100, the remote server 208 then performs an algorithm which takes the patient's selection as an input for determining a second taste test sample. Once the remote server 208 has determined the second taste test sample, the remote server 208 transmits corresponding instructions to the sample selector 202. The process described above in relation to the first sample is then performed for the second sample. This process may be repeated for multiple samples, until the remote server 208 is able to determine the patient's taste sensitivity and recognition based on the patient's responses.

Thus, system 200 enables a fully automated taste test to be performed. Indeed, to undergo the taste test, the patient need only taste the taste test samples provided by the sample selector 202, and provide responses via the taste testing application on the patient terminal 204. This may facilitate the process of performing a taste test, as a tester need not be present to administer the test. As with system 100, the patient is "blind" to the properties of the taste test samples being tested, as the information relating to the taste test samples is stored on the remote server 208. This avoids any risk of bias that may occur, e.g. were the patient to be made aware of the taste modality that was being presented to them.

In one example, a plurality of taste test samples used in a taste test (e.g. a taste test performed by system 100 or 200) includes four sets of taste test samples, each set corresponding to a different taste modality. Each set of taste test samples includes nine different taste test samples corresponding to the corresponding taste modality, each of which is a solution at a different concentration. The plurality of taste test samples may also include one or more samples of distilled water.

In such an example, a first set of taste test samples corresponds to the sweet taste modality, and includes nine solutions of sucrose ($C_{12}H_{22}O_{11}$) in distilled water at concentrations of 1 mM to 100 nM. A second set of taste test samples corresponds to the salt taste modality, and includes nine solutions of sodium chloride (NaCl) in distilled water at concentrations of 1 mM to 100 mM. A third set of taste test samples corresponds to the sour taste modality, and includes nine solutions of citric acid ($C_6H_8O_7$) in distilled water at concentrations of 560 μM to 56 mM. A fourth set of taste test samples corresponds to the bitter taste modality, and includes nine solutions of quinine hydrochloride ($C_{20}H_{29}ClN_2O_4$) in distilled water at concentrations of 0.01 mM to 1 mM. Example concentrations of the solutions for the different taste modalities are shown in Tables 1a-1d below. In other examples, different solutions and different concentrations may be used to test sensitivity to the various taste modalities.

TABLE 1a solution concentrations for sweet taste modality

| | Sweet ($C_{12}H_{22}O_{11}$) | |
|---|---|---|
| Sample name | Concentration | Logarithmic concentration |
| Sweet 1 | 1 mM | −3 |
| Sweet 2 | 1.8 mM | −2.75 |
| Sweet 3 | 3.2 mM | −2.5 |
| Sweet 4 | 5.6 mM | −2.25 |
| Sweet 5 | 10 mM | −2 |
| Sweet 6 | 18 mM | −1.75 |
| Sweet 7 | 32 mM | −1.5 |
| Sweet 8 | 56 mM | −1.25 |
| Sweet 9 | 100 mM | −1 |

TABLE 1b solution concentrations for salt taste modality

| | Salt (NaCl) | |
|---|---|---|
| Sample name | Concentration | Logarithmic concentration |
| Salt 1 | 1 mM | −3 |
| Salt 2 | 1.8 mM | −2.75 |
| Salt 3 | 3.2 mM | −2.5 |
| Salt 4 | 5.6 mM | −2.25 |
| Salt 5 | 10 mM | −2 |
| Salt 6 | 18 mM | −1.75 |
| Salt 7 | 32 mM | −1.5 |
| Salt 8 | 56 mM | −1.25 |
| Salt 9 | 100 mM | −1 |

TABLE 1c solution concentrations for sour taste modality

| | Sour ($C_6H_8O_7$) | |
|---|---|---|
| Sample name | Concentration | Logarithmic concentration |
| Sour 1 | 560 μM | −3.25 |
| Sour 2 | 1 mM | −3 |
| Sour 3 | 1.8 mM | −2.75 |
| Sour 4 | 3.2 mM | −2.5 |
| Sour 5 | 5.6 mM | −2.25 |
| Sour 6 | 10 mM | −2 |
| Sour 7 | 18 mM | −1.75 |
| Sour 8 | 32 mM | −1.5 |
| Sour 9 | 56 mM | −1.25 |

TABLE 1d

| solution concentrations for bitter taste modality | | |
| --- | --- | --- |
| | Bitter ($C_{20}H_{29}ClN_2O_4$) | |
| Sample name | Concentration | Logarithmic concentration |
| Bitter 1 | 0.01 mM | −5 |
| Bitter 2 | 0.018 mM | −4.75 |
| Bitter 3 | 0.032 mM | −4.5 |
| Bitter 4 | 0.056 mM | −4.25 |
| Bitter 5 | 0.1 mM | −4 |
| Bitter 6 | 0.18 mM | −3.75 |
| Bitter 7 | 0.32 mM | −3.5 |
| Bitter 8 | 0.56 mM | −3.25 |
| Bitter 9 | 1 mM | −3 |

Figures 3, 4:
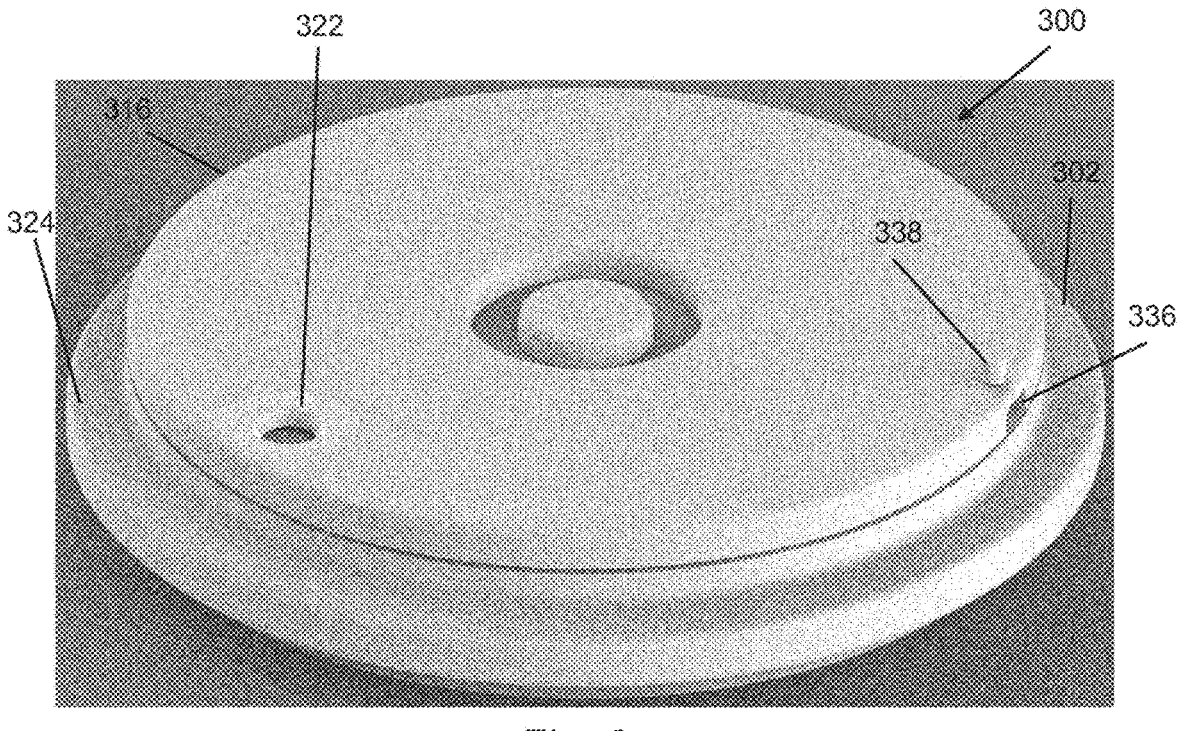
FIG. 3 is a perspective view of a rotatable sample selector that is a drawing of the invention.
FIG. 4 is a perspective view of the sample selector of FIG. 3 with a lid removed.
Figure 5:
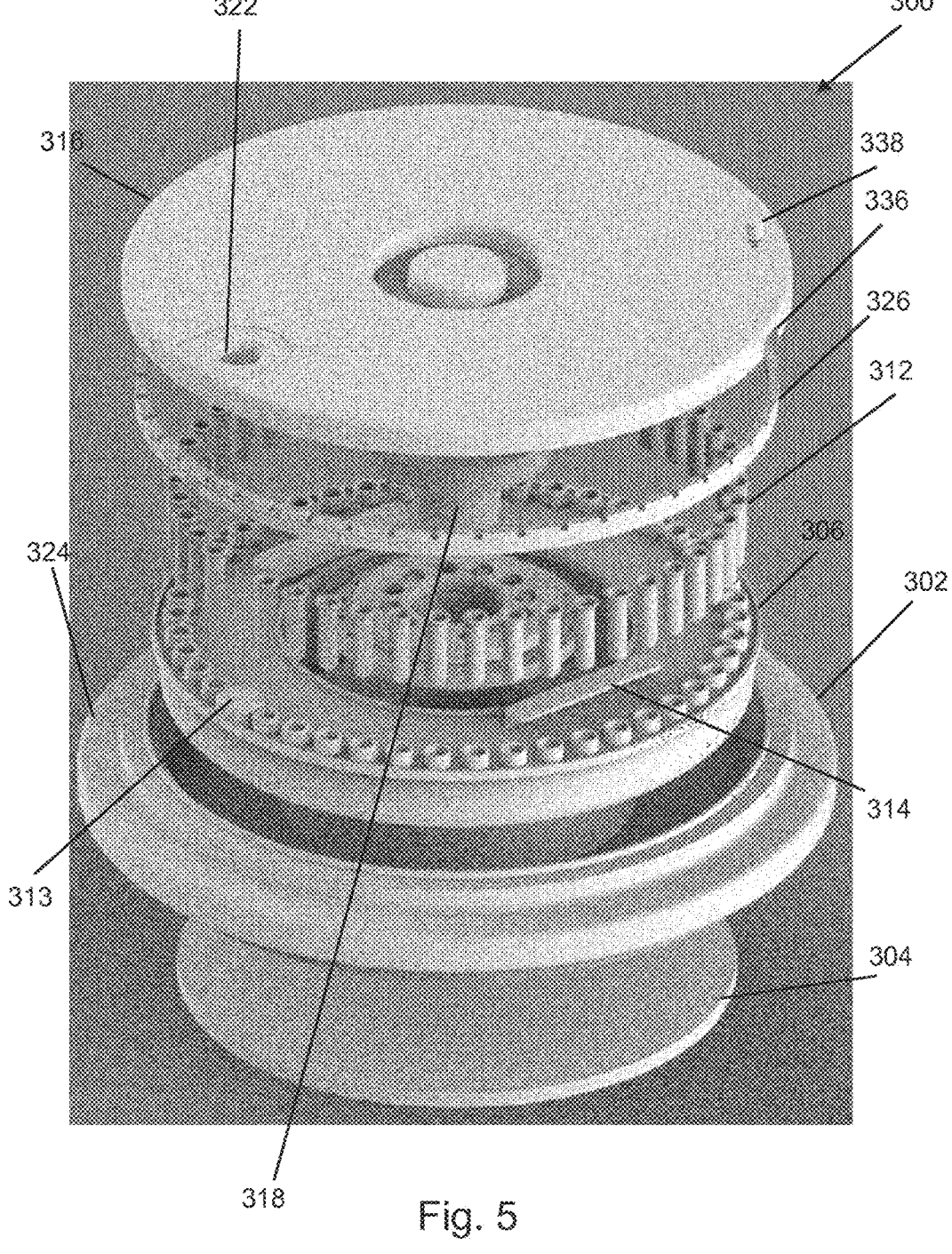
FIG. 5 is an exploded perspective view of the sample selector of FIG. 3.
Figure 6:
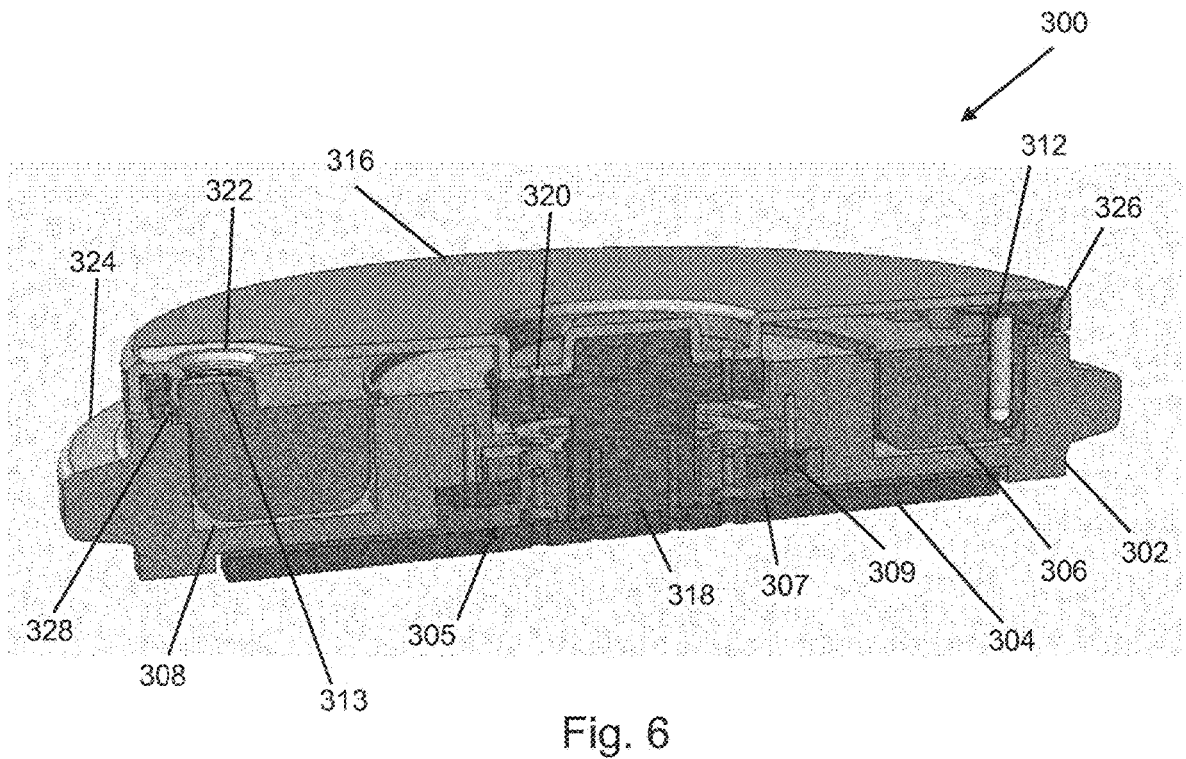
FIG. 6 is a cut-away side view of the sample selector of FIG. 3.
Figure 7:
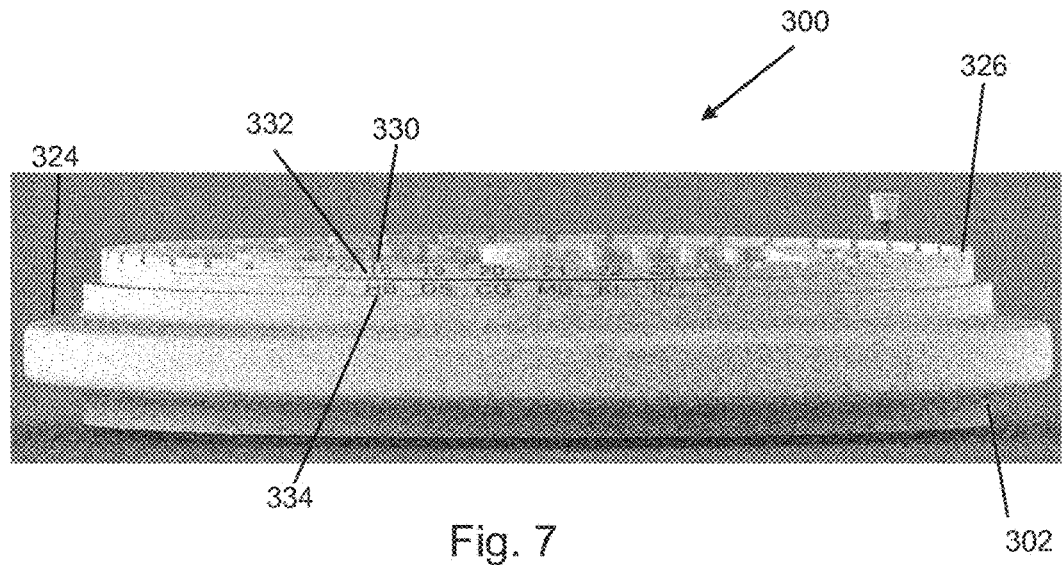
FIG. 7 is a side view of the sample selector of FIG. 3 with the lid removed.

FIGS. 3-5 illustrate a sample selector 300 which may be used in a system of the invention (e.g. system 100 or 200). FIG. 3 shows a perspective view of sample selector 300; FIG. 4 shows a perspective view of sample selector 300 where a lid of the sample selector 300 has been removed; FIG. 5 shows an exploded view of sample selector 300; FIG. 6 shows a cross-sectional view of sample selector 300; and FIG. 7 shows a side view of sample selector 300 where the lid has been removed.

Sample selector 300 comprises a rotatable carousel 302 which is mounted on a base 304 and rotatable relative to the base 304. The carousel 302 is mounted on the base 304 via a slew bearing 305. The slew bearing includes an inner ring 307 which is secured to the base (e.g. via one or more bolts) and an outer ring 309 disposed around the inner ring 307 and rotatable relative to the inner ring 307. The carousel 302 is secured to the outer ring 309 (e.g. via one or more bolts), so that the carousel 302 can be rotated relative to the base 304.

A circular cassette 306 is received in a complementarily shaped groove 308 in the carousel 302, the circular cassette 306 being disposed around an axis of rotation of the carousel 302 relative to the base 304. The circular cassette 306 includes a plurality of sample slots (or holders) 310 for receiving sample containers 312. The sample slots 310 are evenly spaced around a circumference of the circular cassette 306, i.e. an angular separation between adjacent sample slots 310 is constant around the circumference of the circular cassette 306. Additionally, a blank 313 is provided between two adjacent sample slots, instead of another sample slot. The sample slots 310 are arranged on a circle, the centre of which corresponds to the axis of rotation of the carousel 302 relative to the base 304. In the example shown, the circular cassette 306 has forty-five sample slots 310 plus the blank 313. However, different numbers of slots may be provided, depending on the number of taste test samples to be stored. The circular cassette 306 further includes a pair of handles 314 to facilitate removing the circular cassette 306 from the carousel 302. The groove 308 in the carousel 302 includes alignment features that are arranged to engage corresponding alignment features on the circular cassette 306, to ensure proper alignment of the circular cassette 306 when it is mounted in the carousel 302.

In use, the circular cassette 306 may be loaded with a plurality of sample containers 312 before mounting the circular cassette 306 in the carousel 302. This may facilitate loading of samples in the sample selector 302. Using the circular cassette 306 may also facilitate rapidly exchanging samples in the sample selector 302, e.g. when the sample containers are empty, as a used cassette may be rapidly replaced with a preloaded cassette. In the example shown, there is a single circular cassette 306 in which all of the samples are held. However, in other examples, there may be multiple cassettes (or a multi-part cassette), each cassette holding a subset of the samples.

Figure 10:
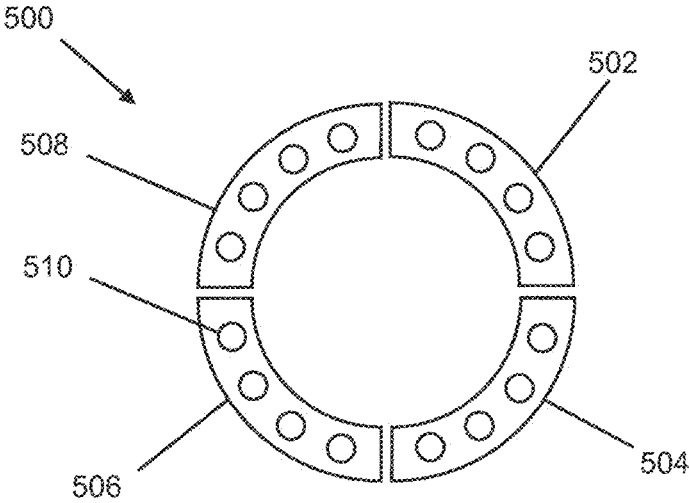
FIG. 10 is a schematic diagram of a multi-part cassette for use in a sample selector of the invention.

FIG. 10 shows an example of a multi-part cassette 500 which may be used in a sample selector of the invention (e.g. sample selector 102, 202, 302). The multi-part cassette 500 includes four cassette parts 502, 504, 506 and 508, each of which includes four sample slots 510 for receiving sample containers, e.g. sample containers 312. In other examples, there may be different numbers of sample slots, depending on the number of samples to be used. The sample slots 510 of the cassette parts are arranged such that when the four cassette parts are mounted in a carousel, the sample slots 510 lie on a circle, the centre of which corresponds to an axis of rotation of the carousel. Each cassette part has alignment features (not shown) arranged to engage cooperating engagement features in the carousel, to ensure that each cassette part is correctly located within the carousel.

Returning to sample selector 300, the sample containers 312 may be any suitable type of container for holding taste test samples. For example, a sample container 312 may be a test tube or "pod" manufactured from high quality virgin polypropylene. Each sample container 312 may contain a different taste test sample. Each sample container 312 includes an opening 315 for inserting a taste test sample into the sample container 312 and accessing the sample in the sample container 312. Each sample container 312 may include a lid (not shown) for closing the opening of the sample container 312 when the sample selector 302 is not in use, to prevent contamination of the sample. However, prior to use of the sample selector 302, all lids must be removed from the sample containers 312.

The sample selector 300 further includes a lid 316 which is mountable over the carousel 302 to cover the circular cassette 306 and any sample containers 312 held therein. When the lid 316 is mounted over the carousel 302, it is held by a central post 318. The central post 318 is secured to the base 304 (e.g. via one or more bolts), and passes through a central bore in the inner ring 307 of the slew bearing 305. The lid 316 includes a set of through holes 320, so that it may be secured to the central post 318 using a set of bolts. However, other means for securing the lid 316 to the central post 318 may also be used. When the lid 316 is mounted on the central post 318, there is a clearance between the carousel 302 and the lid 316, such that the lid 316 is not in contact with the carousel 302. In this manner, the lid 316 does not interfere with the carousel's rotation relative to the base 304. As the lid 316 is secured relative to the base 304 (via the central post 318), rotation of the carousel 302 relative to the base 304 is equivalent to rotation of the carousel 302 relative to the lid 316.

The lid 316 includes an aperture 322 arranged to sequentially expose sample containers 312 held in the circular cassette 306 when the carousel 302 is rotated relative to the base 304. The aperture 322 is positioned so that when the lid 316 is in place, it is disposed above the sample slots 310 in the circular cassette 306. The aperture 322 is dimensioned such that when a sample container 312 is aligned with the aperture 322, contents of that sample container may be accessed via the aperture 322, however all of the other sample containers remain covered by the lid 316 and are not accessible. A user may manually align a desired sample container with the aperture 322 by rotating the carousel 302 relative to the base 304, e.g. by applying a torque to an edge 324 of the carousel 302. A sample container that is aligned with the aperture 322 may be said to be selected. Thus, the rotatable carousel 302 and lid 316 provide a selecting mechanism for selecting a particular sample among the samples stored in the carousel 302.

In use, a particular sample container 312 may be aligned with the aperture 322. Then, a patient taking a taste test may dip a cotton bud or other suitable utensil into the sample container 312 via the aperture to imbue the cotton bud with the taste test sample contained in the sample container. The patient may then place the imbued cotton bud on the tip of their tongue to perform the taste test. When the sample selector 302 is not in use, the blank 313 may be aligned with the aperture 322. The blank 313 is arranged to block the aperture 322 when the blank 313 is aligned with the aperture, to prevent contamination of the sample containers 312.

Figure 8:
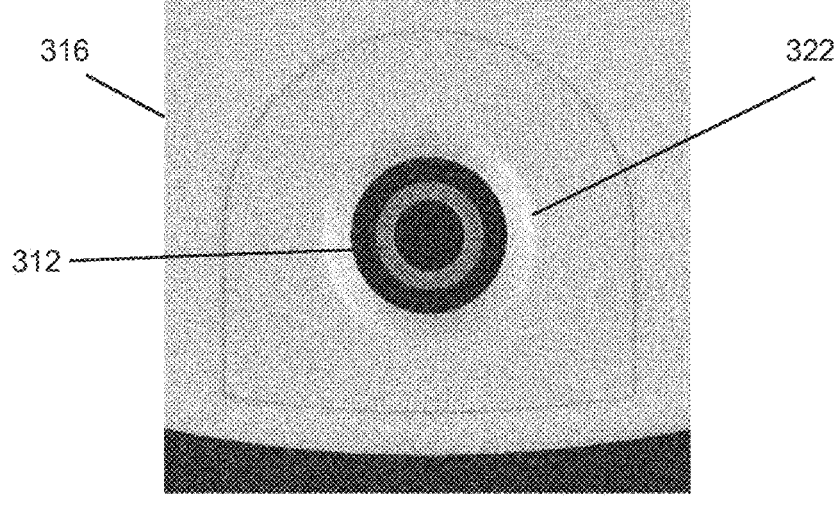
FIG. 8 is a magnified top view of an aperture in the lid of the sample selector showing an available sample.
Figure 9:
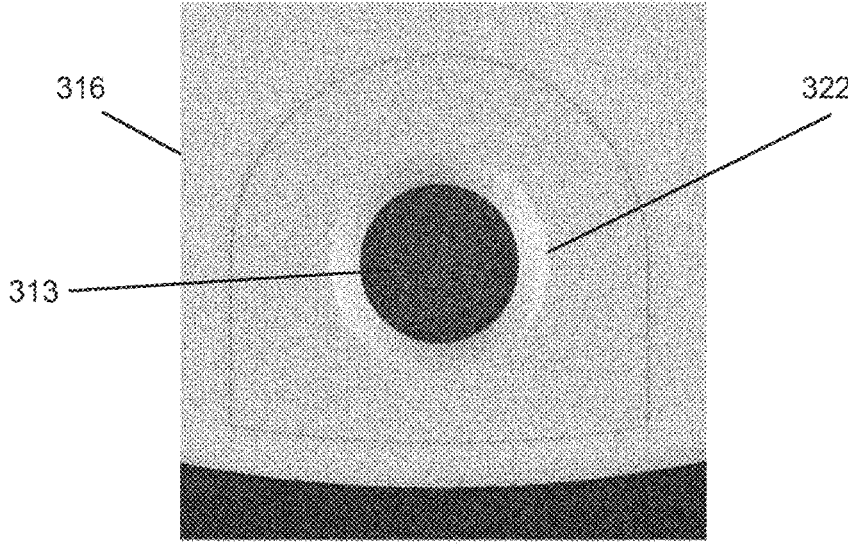
FIG. 9 is a magnified top view of an aperture in the lid of the sample selector showing a block sample.

FIG. 8 shows a close-up view of the aperture 322 when a sample container 312 is aligned with the aperture 322, such that contents of the sample container 312 can be accessed via the aperture 322. FIG. 9 shows a close-up view of the aperture 322 when the blank 313 is aligned with the aperture 322. In this configuration, none of the sample containers 312 are accessible via the aperture 322, as the blank blocks the aperture 322.

The sample selector 300 further includes a sample indicator 326 mounted on the carousel 302. The sample indicator 326 is a ring disposed around an outer edge of the circular cassette 306. The sample indicator 326 is held on a lip 328 of the carousel 302. The indicator 326 includes a plurality of display panels 330, each display panel 330 being associated with a respective one of the sample slots 310. Each display panel 330 includes a sample slot number 332 associated with the corresponding sample slot 310, and a confirmation code 334 associated with the taste test sample contained in a sample container 312 to be placed in the corresponding sample slot 310.

In use, individual sample containers 312 may be inserted into the sample slots 310 in the circular cassette 306. The order in which the sample containers 312 are placed in the sample slots 310 may be based on a predetermined mapping between the taste test samples and the sample slots 310. An example mapping between the sample slots 310 and taste test samples is shown in Table 2 below. The circular cassette 306 may then mounted in the carousel 302. Alignment features on the carousel 302 and the circular cassette 306 ensure that the sample slots 310 are correctly located with respect to their corresponding display panels 330 on the sample indicator 326. In some cases, the sample indicator 326 may be provided on the circular cassette 306 rather than the carousel 302.

The lid 316 includes a window 336 through which a single display panel 330 of the sample indicator 326 is visible. The window 336 and sample indicator 326 are arranged such that when a particular sample slot 310 is aligned with the aperture 322, the display panel 330 corresponding to that sample slot 310 is visible through the window 336 in the lid 316. In this manner, a tester is able to view the position number and confirmation code of the currently selected sample. There is an angular separation between the aperture 322 and the window 336. In the example shown, the angular separation is approximately 120 degrees relative to the rotation axis of the carousel 302, however other angular separations may also be used. In use, a patient may be located next to the aperture 322, so that they can access taste test samples via the aperture 322. A tester may be located next to the window 336 so that the can view the display panel 330 associated with the selected sample. Thus, by providing an angular separation between the aperture 322 and the window 336, a patient may be prevented from seeing the display panels 330. This may avoid a risk of bias due to the patient reading the display panels 330.

The lid 316 further includes a fixing mechanism 338 for fixing the position of the carousel 302 relative to the lid 316. In this example, the fixing mechanism 338 is a screw which is engageable in a threaded hole in the lid 316. Tightening the screw in the threaded hole causes the screw to engage a top surface of the sample indicator 326, which acts to fix the position of the carousel 302 relative to the lid 316. Thus, when a desired sample container 312 is aligned with the aperture 322, the fixing mechanism 338 may be used to prevent further rotation of the carousel 302 relative to the lid 316. Once a taste test has been completed, the fixing mechanism 338 may be released (e.g. by loosening the screw), to allow rotation of the carousel 302.

TABLE 2

Sample slot and confirmation code mapping

| Sample slot number | Confirmation Code | Taste test sample |
|---|---|---|
| 1 | CDB | Sweet 9 |
| 2 | CBD | Salt 9 |
| 3 | IHB | Bitter 9 |
| 4 | JBD | Sour 9 |
| 5 | DEB | Water |
| 6 | JIB | Sweet 8 |
| 7 | BAD | Bitter 8 |
| 8 | GEC | Sour 8 |
| 9 | ACC | Salt 8 |
| 10 | EDC | Sweet 7 |
| 11 | JHC | Bitter 7 |
| 12 | GFB | Sour 7 |
| 13 | IEC | Salt 7 |
| 14 | AAE | Sweet 6 |
| 15 | CIB | Bitter 6 |
| 16 | HBC | Sour 6 |
| 17 | AIC | Salt 6 |
| 18 | CCC | Sweet 5 |
| 19 | ICB | Bitter 5 |
| 20 | GAC | Sour 5 |
| 21 | GHB | Salt 5 |
| 22 | JHD | Sweet 4 |
| 23 | EAD | Bitter 4 |
| 24 | FED | Sour 4 |
| 25 | ADB | Salt 4 |
| 26 | IDD | Sweet 3 |
| 27 | EHC | Bitter 3 |
| 28 | BHD | Sour 3 |
| 29 | DED | Salt 3 |
| 30 | IDC | Sweet 2 |
| 31 | FJD | Bitter 2 |
| 32 | GED | Sour 2 |
| 33 | GGB | Salt 2 |
| 34 | GIC | Sweet 1 |
| 35 | EHD | Bitter 1 |
| 36 | HDC | Sour 1 |
| 37 | IHD | Salt 1 |

Note that the samples referred to in the "Taste test sample" column of Table 2 refer to the samples described in Tables 1a-1d.

In the example described, sample selector 300 is intended to be operated manually. Thus, a tester may receive instructions, e.g. on tester terminal 106 to rotate the carousel 302 until a particular sample slot number 332 is visible via the window 336 in the lid 316. The tester may then read the confirmation code visible through the window, to confirm that the correct sample has been selected (e.g. by entering the confirmation code on the tester terminal 106 from transmission to the remote server 108). Once it has been confirmed that the correct sample has been selected, the patient, may taste the selected sample, e.g. by dipping a cotton bud into the sample container 312 via the aperture 322.

However, sample selector 300 may be adapted to provide automated sample selection, e.g. so that it may be integrated into system 200. For example, sample selector 300 may be provided with a step motor for controlling the position of the carousel 302 relative to the lid 316. The sample selector 300 may be further provided with a local controller that is capable of communicating with a remote server (e.g. remote server 208), to receive instructions from the remote server and transmit data to the server. The local controller may be configured to control the step motor based on instructions received from the remote server to rotate the carousel 302 to a desired position. The sample selector 300 may further include a position sensor for sensing an angular position of the carousel 302, to facilitate controlling the position of the carousel 302. Furthermore, the sample selector 300 may be provided with a sensor for determining the confirmation code associated with a selected sample container 312. For example, the sensor may include a CCD camera for capturing an image of the confirmation code. The local controller may then transmit the image to the remote server which may then interpret the image to determine whether the correct sample has been selected. Other types of sensor are also possible (e.g. barcode scanner, RFID chip reader, etc.).

Figure 11:
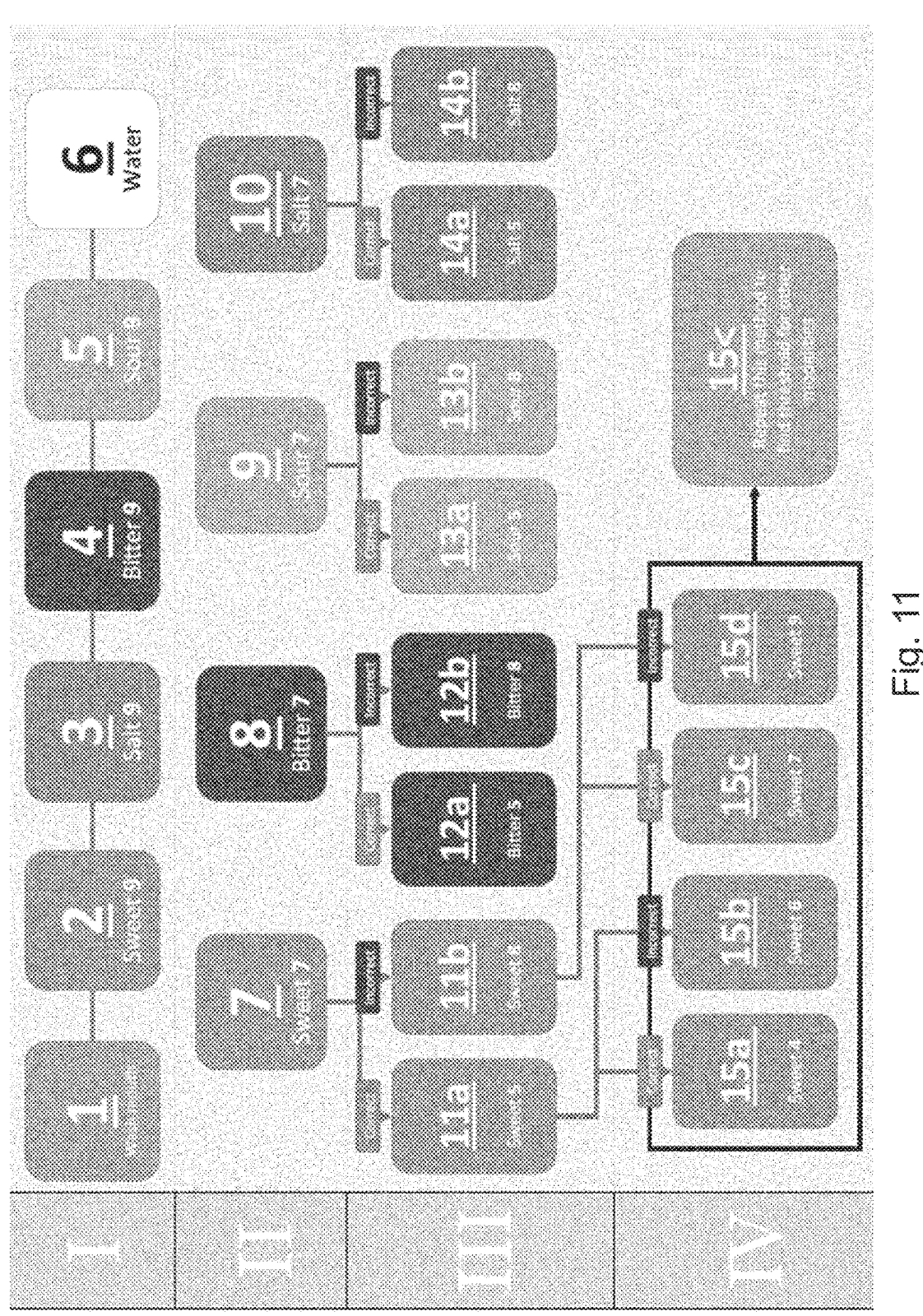
FIG. 11 is a schematic flow diagram showing underlying logic that drives a process for determining a patient's taste sensitivity for each of a plurality of tasting modalities.

We will now describe an algorithm used in a system of the invention for determining a patient's taste sensitivity. The algorithm may, for example, be implemented by system 100 or system 200. The steps of the algorithm are illustrated in FIG. 11. In this example, the algorithm tests the patient's sensitivity to four taste modalities: sweet, salt, sour, bitter. Nine taste test samples at different concentrations are used for each taste modality, corresponding to the samples shown in Tables 1a-1d. The taste test samples may be mounted in the sample selector according to the mapping provided by Table 2.

To start, the patient is prompted to wash their mouth with distilled water (Step 1 in FIG. 11). Subsequently, the patient is made to taste the strongest sample for each taste modality, i.e. sample 9 for each modality, followed by distilled water as indicated by steps 2-6 of FIG. 11. In each of steps 2-6, the patient is informed of the taste modality they are tasting (or, in the case of step 6, that they are tasting water) and asked whether they can identify the taste modality (e.g. via the taste testing application on patient terminal 104, 204). Between each taste test, the patient rinses their mouth with distilled water, e.g. they may be prompted to do so by the taste testing application on patient terminal 104, 204. If a user is unable to identify one of the taste modalities, then the taste test terminates. Otherwise, the test moves on to the next steps.

The following process is followed for each taste modality, as illustrated in steps 7-15 of FIG. 11. The patient is made to taste a sample corresponding to that modality, without being informed of the taste modality that they are testing, and asked to identify the taste modality of the sample, e.g. via the taste testing application on patient terminal 104, 204. If the patient correctly identifies the taste modality, then the next time that taste modality is tested, the patient is made to taste a sample having a lower concentration. However, if the patient incorrectly identifies the taste modality, then the next time that taste modality is tested, the patient is made to taste a sample having a higher concentration. For example, as shown in FIG. 11, at step 7 of FIG. 11, the patient is made to taste sample Sweet 7. If the patient correctly identifies the taste modality (sweet), then the next time the sweet taste modality is tested, the algorithm selects a sample having a lower concentration, e.g. sample Sweet 5. If the patient incorrectly identifies the taste modality, then the next time the sweet taste modality is tested, the algorithm selects a sample having a higher concentration, e.g. sample Sweet 8.

The algorithm may be configured to move in increments of one between samples for a given modality. For example, where a currently tested sample is Sweet 7, the next sample for the sweet modality may be Sweet 6 or Sweet 8, depending on the patient's response. Alternatively, the algorithm may be configured to move in different sized increments depending on variables such as the concentration of the currently tested sample and/or the number of samples already tested. For example, at the beginning of a taste test, the algorithm may move in larger sized increments (e.g. it may go from Sweet 7 directly to Sweet 5, as in FIG. 11). Then, when a multiple samples of a given modality have been tested, the algorithm may be configured to move in smaller sized increments. Such a configuration may enable the patient's sensitivity to a given taste modality to be determined more rapidly.

Importantly, the taste modalities are tested is a pseudo-random order. In other words, a given taste modality is not tested all the way through before moving on to the next modality; rather a sample of a first modality is tested (e.g. sweet), then a sample of a pseudo-randomly selected modality is tested next. Thus, steps 7-10 and 11-14 of FIG. 11 are performed in a pseudo-random order. The order in which taste modalities are tested is said to be pseudo-random, as the algorithm randomly selects the next taste modality to be tested but avoids testing the sweet taste modality after the sour taste modality. This is because the inventors have found that testing the sour taste modality before the sweet taste modality results in patients' ability to taste the sweet modality to be reduced. The patient may also be made to taste water randomly between taste modalities. By testing the different taste modalities in a pseudo-random order, the inventors have found that accuracy of the test results may be improved. In particular, such a pseudo-random mixing of taste modalities may minimise adaptation of the patient to a particular taste modality, and reduce guessing by the patient.

The algorithm determines a sensitivity level for a given taste modality once a patient has correctly identified that taste modality for a particular concentration three times, having also incorrectly answered three times for the next lowest concentration of that taste modality. The three correct answers need not be in a row, e.g. they can be interrupted by incorrect answers for the particular concentration, or correct answers for the next lowest concentration. The particular concentration thus identified by the algorithm may correspond to the patient's sensitivity for that taste modality. Once the algorithm has determined a sensitivity level in this manner for each taste modality, it may output the sensitivity level for each taste modality.

If the sensitivity level for a particular taste modality has been determined, the algorithm is configured to continue mixing that taste modality into the test in a pseudo-random manner, as discussed above. In this manner, the test may still feel random to the patient.

If, during the test, the patient is unable to correctly identify a taste modality at its strongest concentration (i.e. sample 9 for each modality) three times, then the algorithm may be configured to terminate the test. For a given modality, if the patient answers correctly for sample 3, the algorithm may be configured to get the patient to taste the water sample (e.g. the first time this happens), to remind them of the taste.

Additionally, the algorithm may be configured to enable a patient to ask for a reminder of what water tastes like, e.g. there may be a selectable option in the taste testing application on the patient terminal 104, 204 for making water the next sample to be tested. If a patient is able to correctly identify the taste modality sample 1 three times, the algorithm may be configured to terminate the test.

If, during the test, a patient starts to get answers wrong at increasingly high sample numbers for a particular taste modality, e.g. where they previously gave correct answers, the algorithm may be configured to give the patient a reminder of what that taste modality tastes like. For example, the algorithm may be configured to select sample 9 of that modality as the next sample, and indicate to the patient the corresponding taste modality (e.g. via the taste testing application on the patient terminal 104, 204).

Between each taste test sample tested by the patient, the patient should rinse their mouth with distilled water. The taste testing application on the patient terminal 106 may prompt the patient to do this at appropriate moments during the test.

The algorithm described above may, for example, be executed by remote server 108 or 208. The process of selecting the next sample to the patient may be performed at the remote server, based on taste test results transmitted from the patient terminal 104, 204. Once the algorithm has determined the next sample to be tested, the remote server may transmit corresponding instructions, e.g. to the tester terminal 106 or the sample selector 202. The algorithm on the remote server may control the test tasting application running on the patient terminal 104, 204 so that the patient is presented with relevant information and selectable options at appropriate moments during the taste test. Similarly, where there is a tester terminal (as in system 100), the algorithm on the remote server may control the test tasting application running on the tester terminal 106 to display relevant information and options.

The invention claimed is:

1. A sample dispensing system for testing a patient's taste sensitivity, the system comprising:
    a sample selector comprising:
        an array of tasting samples, each tasting sample being one of a plurality of tasting modalities at a predetermined concentration, wherein the array of tasting samples includes tasting samples at a plurality of different concentrations for at least one of the tasting modalities, and
        a selection mechanism configured to indicate one of the tasting samples from the array of tasting samples;
    a test controller configured to:
        generate a sequence of sample indicators for operating the selection mechanism to indicate a sequence of tasting samples;
        receive a patient response to an indicated tasting sample;
        adapt the sequence of sample indicators based on the received patient response; and
        determine a taste sensitivity threshold for the patient using received patient responses corresponding to the adapted sequence of sample indicators.

2. The sample dispensing system of claim 1, wherein the test controller is configured to determine a subsequent sample indicator in the sequence of sample indicators for a given tasting modality based on the patient's response to a previous tasting sample having that tasting modality.

3. The sample dispensing system of claim 1, wherein the test controller includes a memory storing a correspondence table that matches each sample indicator to the tasting modality and the predetermined concentration of the tasting sample in that array that corresponds to that sample indicator, and
    wherein the test controller is configured to determine the subsequent sample indicator in the sequence of sample indicators for a given tasting modality by selecting a sample indicator for that tasting modality that has a higher predetermined concentration if the patient response incorrectly identified the previous sample for that tasting modality, or selecting a sample indicator for that tasting modality that has a lower predetermined concentration if the patient response correctly identified the previous sample for that tasting modality.

4. The sample dispensing system of claim 1, wherein the test controller is configured to judge whether or not each received patient response correctly identifies a tasting modality of the corresponding presented tasting sample.

5. The sample dispensing system of claim 1, wherein the test controller is configured to communicate the sample indicators in sequence one-by-one.

6. The sample dispensing system of claim 1, wherein the array of tasting samples comprises tasting samples for each of the plurality of tasting modalities, and the sequence of sample indicators mixes the tasting modalities in a pseudo random order.

7. The sample dispensing system of claim 1, wherein the test controller is a network-enabled computing device.

8. The sample dispensing system of claim 7, wherein the sample selector includes a communication module in communication with the test controller to receive the sequence of sample indicators.

9. The sample dispensing system of claim 8, wherein the selection mechanism is automatically controllable based on the received sequence of sample indicators.

10. The sample dispensing system of claim 1, further comprising a tester terminal configured to receive the sequence of sample indicators, wherein the selection mechanism is manually controllable based on the sequence of sample indicators received at the tester terminal.

11. The sample dispensing system of claim 1, wherein the selection mechanism is configured to manipulate the array of tasting samples to move the one of the tasting samples that is to be presented to a sampling location on the sample selector.

12. The sample dispensing system of claim 11, wherein the array of tasting samples comprises a circle of tasting samples arranged on a rotatable carousel, and wherein the sampling location is at a given angular position on the sample selector.

13. The sample dispensing system of claim 11, wherein the sample selector includes a cover arranged to hide the array of testing samples except at the sampling location.

14. The sample dispensing system of claim 11, wherein each tasting sample in the array of tasting samples has a sample indicator and a confirmation code associated with it, wherein the sample indicator and confirmation code for a given tasting sample are readable when that tasting sample is at the sampling location.

15. The sample dispensing system of claim 1, wherein the array of tasting samples is disposed in a cassette that is removably mountable in the selection mechanism.

16. The sample dispensing system of claim 15, wherein the cassette and selection mechanism comprise cooperating engagement features, whereby the cassette is mountable in the selection mechanism in a predetermined orientation.

17. The sample dispensing system of claim 15, wherein the cassette includes an identifier for communicating to the test controller, and wherein the test controller is arranged to determine a correspondence table for the array in the cassette using the identifier, wherein the correspondence table is a data structure that matches each sample indicator to the tasting modality and the predetermined concentration of the tasting sample in the array that corresponds to that sample indicator.

* * * * *